US011554038B2

United States Patent
O'Flynn et al.

(10) Patent No.: US 11,554,038 B2
(45) Date of Patent: Jan. 17, 2023

(54) RECEPTACLES HAVING TEAR-CONTROLLING FEATURES

(71) Applicant: Hollister Incorporated, Libertyville, IL (US)

(72) Inventors: Padraig M. O'Flynn, Ballina (IE); Dean W. Hacker, Ballinrobe (IE); Vincent Naughton, Sligo (IE); Daniel E. O'Brien, Calry (IE); Richard Meaney, Wesport (IE); Michael G. Murray, Ballina (IE); Dmitry Sheremetiev, Oranmore (IE); Adam J. Foley, Swords (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 16/762,437

(22) PCT Filed: Nov. 16, 2018

(86) PCT No.: PCT/US2018/061544
§ 371 (c)(1),
(2) Date: May 7, 2020

(87) PCT Pub. No.: WO2019/099845
PCT Pub. Date: May 23, 2019

(65) Prior Publication Data
US 2020/0360174 A1 Nov. 19, 2020

Related U.S. Application Data

(60) Provisional application No. 62/587,682, filed on Nov. 17, 2017.

(51) Int. Cl.
*A61F 5/451* (2006.01)
*A61F 5/44* (2006.01)

(52) U.S. Cl.
CPC ............ *A61F 5/451* (2013.01); *A61F 5/4404* (2013.01)

(58) Field of Classification Search
CPC ...... A61F 5/451; A61F 5/4404; A61F 5/4405; A61F 5/44
See application file for complete search history.

(56) References Cited

U.S. PATENT DOCUMENTS 3,724,461 A * 4/1973 Eisenberg ........... A61M 3/0245
                                                        604/262
4,619,650 A * 10/1986 Wisdom .................... A61J 1/10
                                                        604/408

(Continued)

FOREIGN PATENT DOCUMENTS

DE   102009041251 A1   3/2011
EP       1136379 A1    9/2001

(Continued)

OTHER PUBLICATIONS

International Search Report for PCT/US2018/061544; dated Mar. 6, 2019; European Patent Office, Netherlands.
Written Opinion of the International Searching Authority for PCT/US2018/061544; dated May 23, 2019; European Patent Office, Munich, Germany.

*Primary Examiner* — Tatyana Zalukaeva
*Assistant Examiner* — Hans Kaliher
(74) *Attorney, Agent, or Firm* — Cook Alex Ltd.

(57) ABSTRACT

A urinary collection receptacle (10,50,650) with a handle seal (22,52,654) defining a handle opening is provided with one or more tear-controlling features to prevent a user from tearing through the handle seal when creating a spout to empty urine. The receptacle is be configured to require a user to create a generally linear tear (30) that extends from one edge (16) of the bag to the opposite edge (18) without passing through the handle seal. Alternatively a tear-stop- (Continued)

ping formation (62) is positioned adjacent to the handle seal to terminate a fear propagating toward the handle seal. Alternatively, a tear-starting formation (652) is positioned adjacent to the handle seal to direct a tear away from the handle seal. Such a receptacle further includes a frangible region that can be broken to dissociate a torn portion of the receptacle from the remainder of the receptacle.

9 Claims, 8 Drawing Sheets

(56) References Cited

U.S. PATENT DOCUMENTS

| | | | |
|---|---|---|---|
| 4,696,404 A | 9/1987 | Corella | |
| 6,578,709 B1* | 6/2003 | Kavanagh | A61M 25/002 604/328 |
| 6,849,070 B1* | 2/2005 | Hansen | A61F 5/44 604/328 |
| 7,094,220 B2* | 8/2006 | Tanghoj | A61M 39/22 604/177 |
| 2002/0103460 A1 | 8/2002 | Kubalak et al. | |
| 2003/0130646 A1* | 7/2003 | Kubalak | A61F 5/4404 604/544 |
| 2004/0236293 A1* | 11/2004 | Tanghoj | A61F 5/44 604/327 |
| 2009/0163884 A1* | 6/2009 | Kull-Osterlin | A61M 25/002 53/461 |
| 2011/0064338 A1* | 3/2011 | Surdziel | B65D 75/5816 383/207 |
| 2011/0213343 A1* | 9/2011 | Tanghoj | A61F 5/44 604/544 |
| 2015/0105756 A1* | 4/2015 | O'Brien | A61M 25/0017 604/544 |
| 2016/0088983 A1* | 3/2016 | Cailleteau | B65D 33/007 4/144.1 |
| 2021/0212175 A1* | 7/2021 | Reid, Jr. | B22F 12/13 |

FOREIGN PATENT DOCUMENTS

| | | |
|---|---|---|
| EP | 0700280 B1 | 8/2003 |
| EP | 1420731 A2 | 5/2004 |
| EP | 0861668 B1 | 2/2005 |
| EP | 1357868 B1 | 9/2006 |
| EP | 1458627 B1 | 4/2007 |
| EP | 1596784 B1 | 8/2007 |
| EP | 1695678 B1 | 8/2007 |
| EP | 1757251 B1 | 6/2010 |
| EP | 1855628 B1 | 8/2010 |
| EP | 2072075 B1 | 8/2010 |
| EP | 0815812 B1 | 4/2011 |
| EP | 1557145 B1 | 5/2011 |
| EP | 2257481 B1 | 8/2011 |
| EP | 1529503 B1 | 10/2011 |
| EP | 2325097 B1 | 3/2013 |
| EP | 2429467 B1 | 7/2014 |
| EP | 2480462 B1 | 4/2015 |
| GB | 2223736 A | 4/1990 |
| GB | 2301777 B | 4/1997 |
| GB | 2313061 A | 11/1997 |
| GB | 2314509 B | 9/1998 |
| GB | 2473546 B | 11/2011 |
| GB | 2482992 B | 5/2012 |

\* cited by examiner

RECEPTACLES HAVING TEAR-CONTROLLING FEATURES

CROSS-REFERENCE TO RELATED APPLICATIONS

This application is a National Stage of PCT International Application No. PCT/US2018/061544, filed Nov. 16, 2018 which claims the benefit of and priority to U.S. Provisional Patent Application No. 62/587,682, filed Nov. 17, 2017, the disclosures of all of which are hereby incorporated by reference in their entireties.

FIELD OF THE DISCLOSURE

The present disclosure is generally related to packaging and/or receptacles and more particularly to packages and/or receptacles having tear-controlling features. Even more particularly, the present disclosure is directed to receptacles such as flexible bags for collecting and disposing of waste, such as urine. Still more particularly, the present disclosure is directed to urine collection containers used with a urinary catheter such as, but not limited to, an intermittent urinary catheter wherein the container includes tear-controlling and/or tear-stopping features.

BACKGROUND

Intermittent catheterization is a good option for many people who suffer from various abnormalities of the urinary system. Those with such abnormalities often find it desirable to use individually-packaged, sterile catheter assemblies designed for a single use. These catheter assemblies typically include a catheter that is advanced into the urethra to drain urine therefrom. The urine flows through the catheter and into a waste bag in fluid communication with the catheter. Urine is emptied from the bag and then the bag is disposed of.

Figure 1:
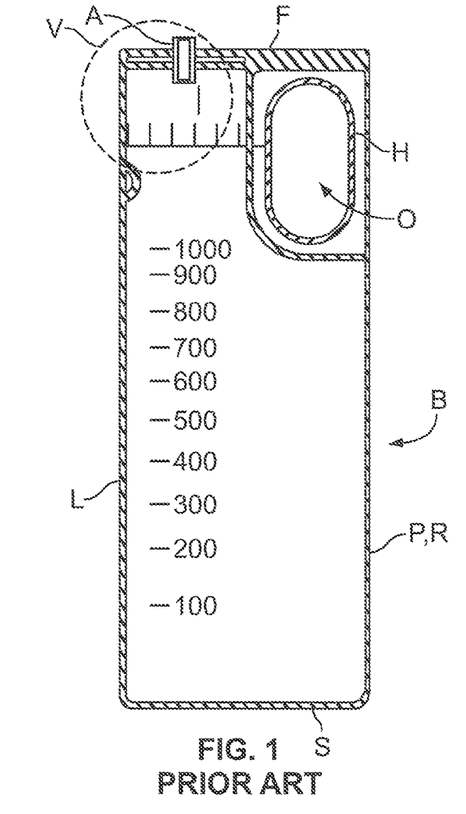
FIG. 1 is front elevational view of a urinary collection bag according to conventional design.

Urinary collection bags may be differently configured, including the configuration shown in FIG. 1. In the embodiment of FIG. 1, a urinary collection bag B is formed of flexible first and second opposing walls defined by first and second sheet materials or by a single flexible sheet material folded in half in a V-shape format, which are joined about their perimeters at a perimeter seal P to define opposing edges L and R and opposing ends F and S. A handle seal H is defined adjacent to an intersection of one of the edges R and one of the ends F, which is typically the end F through which urine flows into the bag B. The handle seal H defines a handle opening O, into which a user may place one or more digits for handling and manipulating the bag B. Bag B includes a port A that defines a flow path into bag B and serves as an attachment point for the non-insertable end of a catheter.

As shown in FIG. 1, urine collection bag B may also include an anti-reflux valve V including a series of discrete tacks or welds spaced along the edge of anti-reflux valve V, as described in U.S. Patent Application Publication US2015/0105756, the contents of which are incorporated herein by reference.

According to one method of using the bag 13 of FIG. 1, the user creates a tear T in the bag B (FIG. 2) to create a spout for emptying urine from the bag B (e.g., into a toilet), while the bag B is separately disposed of (e.g., in a garbage can).

Figure 2:
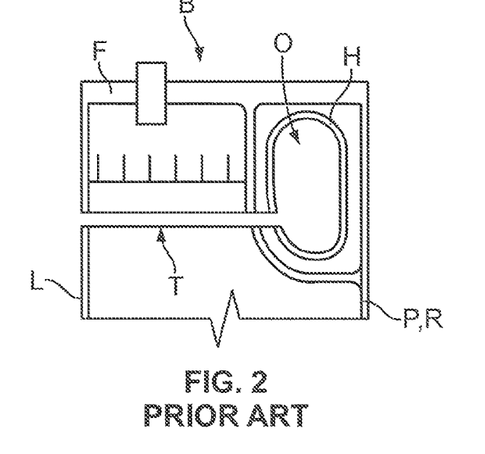
FIG. 2 is a detail view of a portion of the urinary collection bag of FIG. showing a tear extending through a handle seal of the bag.

FIG. 2 illustrates a risk of using such a conventional bag B, which is that the tear T created by the user may extend from an edge L to and through the handle seal H. If such a tear T is created, then the handle opening O becomes unusable, which may lead to the user dropping the bag B or otherwise allowing urine to spill out of the bag B. Accordingly, it would be advantageous to provide a urinary collection bag or receptacle that decreases the risk of a user tearing through the handle seal.

SUMMARY

There are several aspects of the present subject matter which may be embodied separately or together in the devices, systems, and/or methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a receptacle includes first and second opposing walls, each having a perimeter, with a perimeter seal joining at least a portion of the perimeters. A handle seal joins the first wall to the second wall and defines a handle opening. The receptacle further includes a tear-starting formation defined in the perimeter seal and a tear-stopping formation. The tear-stopping formation is positioned between the tear-starting formation and at least a portion of the handle seal and is configured to terminate a tear e ending from the tear-starting formation toward the handle seal.

In another aspect, a receptacle includes first and second flexible walls, each having a perimeter, with a perimeter seal joining at least a portion of the perimeters to define a pair of opposing edges and a pair of opposing ends, A port extends through one of the ends. A handle seal joins the first flexible wall to the second flexible walls and defines a handle opening. A tear-starting formation is defined in the perimeter seal and configured to be used to create a generally linear tear extending from one of the edges to the other edge and positioned between the port and the handle seal.

In yet another aspect, a receptacle includes first and second flexible walls, each having a perimeter, with a perimeter seal joining at least a portion of the perimeters. A handle seal joins the first sheet material to the second sheet material and defines a handle opening. A tear starting formation is positioned adjacent to the handle seal and configured to be used to create a generally linear tear extending away from the handle seal and to the perimeter seal.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims. For example, while the embodiments disclosed herein are described in the context of a urinary collection bag of catheter assembly and, more particularly, a urinary collection bag of an intermittent catheter assembly, it will be understood that tear-controlling and tear-stopping features may be employed in receptacles that are used outside of the catheter field and, for that matter, outside of the medical field. The tear-controlling and tear-stopping features described herein may be used in the packaging of food and beverage products as described, for example, in U.S. Patent Application Publication US2011/0064338. Accordingly, the term "receptacle" as used herein includes, without limitation, containers, collection bags, pouches and packages.

The bags/receptacles described below may include an anti-reflux valve (designated as "V" in FIG. 1) and a port (designated as "A" in FIG. 1). Tear lines are generally shown as broken lines that extend across at least a part of bag/receptacle, and the direction of a tear is generally indicated by an arrow.

Figure 3:
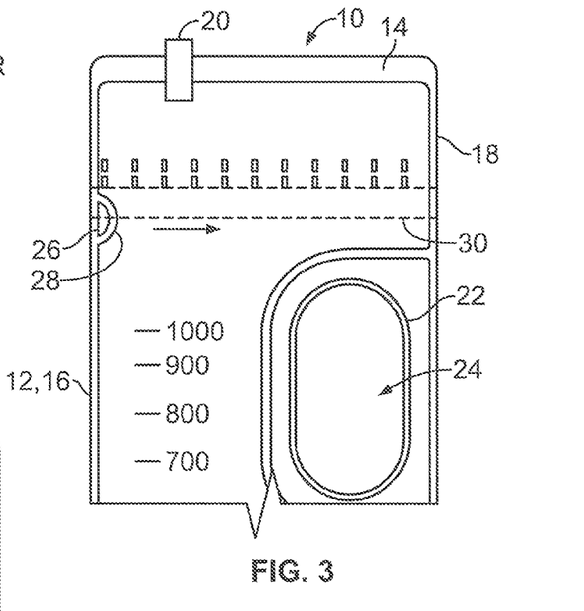
FIG. 3 is a detail view of a portion of a urinary collection bag or other receptacle according to an aspect of the present disclosure.

FIG. 3 shows a portion of a urinary collection bag or receptacle 10 that decreases the risk of tearing through a handle seal. In the embodiment of FIG. 3, the bag 10 is formed of first and second flexible walls defined by first and second sheet materials, or a single flexible sheet material folded in half in a V-shape format, each of the walls having a perimeter. The sheet material(s) defining the walls may be formed of a linear tear polymer film to allow for effortless (e.g., requiring less than 5 N of force), straight-line tearing across the bag 10, as will be described in greater detail herein. Examples of sheet materials suitable for straight-line tearing of the bags or receptacles described herein and shown, for example, in FIGS. 3-31 include linear tear polyethylene, ethylene vinyl acetate.

At least a portion of the perimeter of the first flexible wall is joined to at least a portion of the perimeter of the second flexible wall by a perimeter seal 12 (e.g., a heat seal or seal formed using an adhesive or the like), which defines opposing ends (only one of which ends 14 is visible in FIG. 3) and opposing edges 16 and 18. One of the ends 14 of the bag 10 includes a port 20 extending through the peripheral seal 12 to allow urine to flow into the bag 10 from a urinary catheter.

A handle seal 22 joins the first and second walls, to define a handle opening 24, as in the bag B of FIGS. 1 and 2, However, unlike the bag B of FIGS. 1 and 2, the handle seal 22 and handle opening 24 are spaced from the end 14 of the bag 10 at which the port 20 is located, rather than being positioned directly adjacent to that end.

A tear-starting formation 26 is defined in one of the edges 16, 18 of the bag 10. In the illustrated embodiment, the tear-starting formation 26 is configured as an opening passing through the first and second flexible walls and defined in part by a formation seal 28 between the walls. In other embodiments, the tear-starting formation 26 may be differently configured (e.g., defined as a notch or slit in an edge 16, 18 of the bag 10) without departing from the scope of the present disclosure. Regardless of the particular configuration of the tear-starting formation 26, it is weaker than the other portions of the peripheral seal 12, which allows a user to create a generally linear tear along a tear line 30 (which may be printed onto one or both of the sheet materials) starting at the tear-starting formation 26.

The tear-starting formation 26 is positioned between the port 20 and the handle seal 22, such that a generally linear tear created by a user will extend from the tear-starting formation 26 at one of the edges 16 to the opposite edge 18. By positioning the tear-starting formation 26 closer to the end 14 of the bag 10 having the port 20 than the handle seal 22, the tear created by the user avoids the handle seal 22, thereby keeping the handle opening 24 intact. Accordingly, the user may completely tear off the end 14 of the bag 10 to create a spout for emptying urine from the bag 10 without tearing through the handle seal 22.

Figure 4:
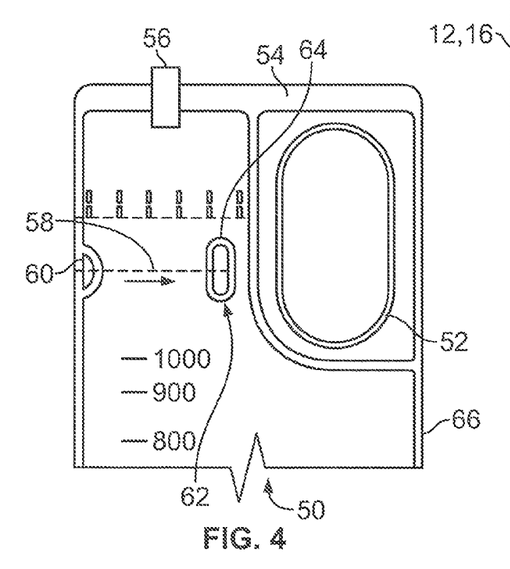
FIG. 4 is a detail view of a portion of another embodiment of a urinary collection bag or other receptacle according to an aspect of the present disclosure.

FIG. 4 shows a portion of another embodiment of a urinary collection bag or other receptacle 50 according to an aspect of the present disclosure. The bag 50 of FIG. 4 is configured similarly to the bag 10 of FIG. 3, except for the handle seal 52 being positioned directly adjacent to the end 54 of the bag 50 at which the port 56 is positioned (as in the bag B of FIGS. 1 and 2). With the handle seal 52 positioned adjacent to the end 54 of the bag 50, the tear line 58 extends from the tear-starting formation 60 toward the handle seal 52. To prevent a user from tearing through the handle seal 52, a tear-stopping formation 62 is positioned between the tear-starting formation 60 and at least a portion of the handle seal 52 (preferably being positioned along the tear line 58). The tear-stopping formation 62 provides a user with a visual indication as to when to stop tearing the bag 50, along with providing haptic feedback due to a sudden change (an increase at a formation seal 64, followed by a decrease if the user tears through the formation seal 64) in tear resistance.

In the illustrated embodiment, the tear-stopping formation 62 is configured as an opening passing through the sheet materials and at least partially defined by a formation seal 64 joining the sheet materials, but the tear-stopping formation 62 may be differently configured (as will be described in greater detail herein) without departing from the scope of the present disclosure. The tear-stopping formation 62 of FIG. 4 is completely separated from the perimeter seal 66 and from the handle seal 52 by unsealed sections of the bag 50 in which the sheet materials are not joined to each other. A tear-stopping formation that is so configured may be referred to as an "isolated" tear-stopping formation because it is isolated from, rather than being adjoined to, the perimeter seal and the handle seal. Where the tear-stopping formation (in this or other embodiments described herein) is an opening, such opening may be oval-shaped, circular or otherwise configured.

Figure 5:
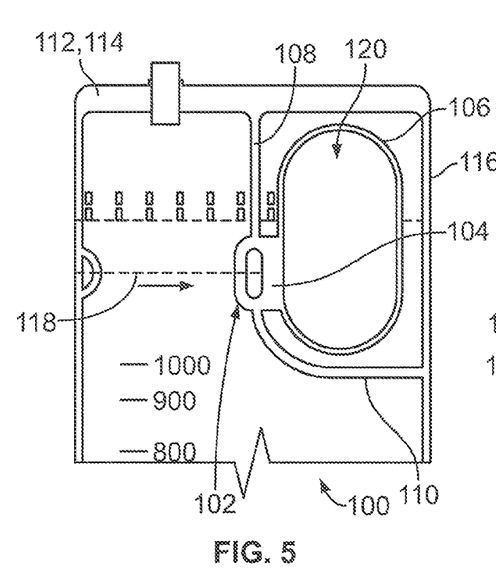
FIG. 5 is a detail view of a portion of yet another embodiment of a urinary collection bag or other receptacle according to an aspect of the present disclosure.

In other embodiments, as in the embodiments of FIGS. 5-9, the tear-stopping formation may be joined to the perimeter seal and/or to the handle seal by an adjoining seal, which joins the sheet materials together. A tear-stopping formation that is so configured may be referred to as an "adjoined" tear-stopping formation because it includes a formation seal that is joined to one of the other seals of the bag. For example, FIG. 5 shows a bag 100 in which a tear-stopping formation 102 is provided generally in accordance with the preceding description of the tear-stopping formation 62 of FIG. 4 (e.g., configured as an opening passing through the sheet materials, but includes an adjoining seal 104 extending from the handle seal 106 to the tear-stopping formation 102. Two other adjoining seals 108 and 110 extend from the perimeter seal 112, with one adjoining seal 108 extending from the end 114 and the other adjoining seal 110 extending from the edge 116. It will be seen that the first adjoining seal 104 extends along the tear line 118. The tear resistance of sealed layers of polymer film is greater than the tear resistance of unsealed layers of polymer film, meaning that the tear-stopping formation 102 of FIG. 5 may be safely placed closer to the handle opening 120 than the tear-stopping formation 62 of FIG. 4 because the first adjoining seal 104 provides greater tear resistance than the unsealed section between the tear-stopping formation 62 and the handle seal 52 of FIG. 4.

Figure 6:
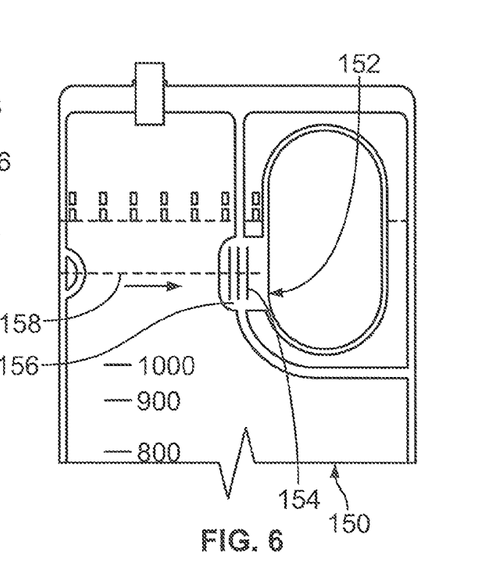
FIG. 6 is detail view of a portion of another embodiment of a urinary collection bag or other receptacle according to an aspect of the present disclosure.

The bag 150 of FIG. 6 has a tear-stopping formation 152 that is a variation of the tear-stopping formation 102 of FIG. 6. In the embodiment of FIG. 6, rather than being defined by a single opening, the tear-stopping formation 152 is defined by a plurality of slits 154 through a formation seal 156. In the illustrated embodiment, the tear-stopping formation 152 includes three parallel slits 154 oriented perpendicular to the tear line 158, but it is within the scope of the present disclosure for a tear-stopping formation to include one or two or more than three slits and/or for the slits to be oriented non-perpendicularly to the tear line 158, Further, if multiple slits are provided, the slits may be differently configured and may be oriented at an angle with respect to each other, rather than being parallel. A tear-stopping formation comprising one or more slits defined in a formation seal provides the same function as a tear-stopping formation configured as an opening or a hole surrounded by a formation seal, but slightly different visual and haptic indicia to a user. It should be understood that a tear-stopping formation having one or more slits defined in a formation seal may be provided as an adjoined tear-stopping formation (as in FIG. 6) or as an isolated tear-stopping formation.

Figure 7:
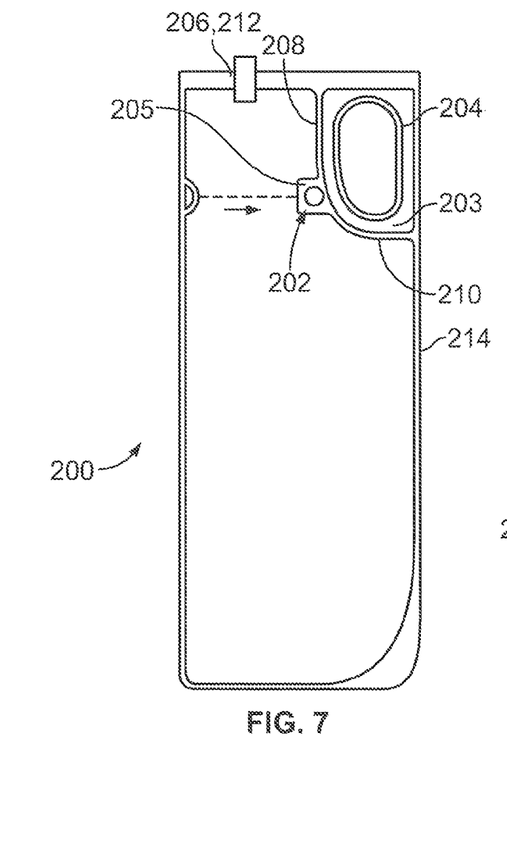
FIG. 7 is a front elevational view of another embodiment of a urinary collection bag or other receptacle according to an aspect of the present disclosure.

The bag 200 of FIG. 7 has a tear-stopping formation 202 that is another variation of the tear-stopping formation 102 of FIG. 5. In the embodiment of FIG. 7, rather than the tear-stopping formation 202 being adjoined to the handle seal 204 and to the peripheral seal 206, it includes only adjoining seals 208 and 210 joining it to the peripheral seal 206 (at the end 212 and at the edge 214, respectively), with an unsealed section 203 between the tear-stopping formation 202 and the handle seal 204. Due to the omission of an adjoining seal between the tear-stopping formation 202 and the handle seal 204, it may be advantageous for the tear-stopping formation 202 to be spaced farther from the handle seal 204 than in FIG. 5, due to the lower tear resistance of the hag 200 between the tear-stopping formation 202 and the handle seal 204. Tear stopping formation 202 may be configured as an opening passing through the sheet materials and at least partially defined by a surrounding seal 205 and the confluence of adjoining seals 208 and 210.

Figure 8:
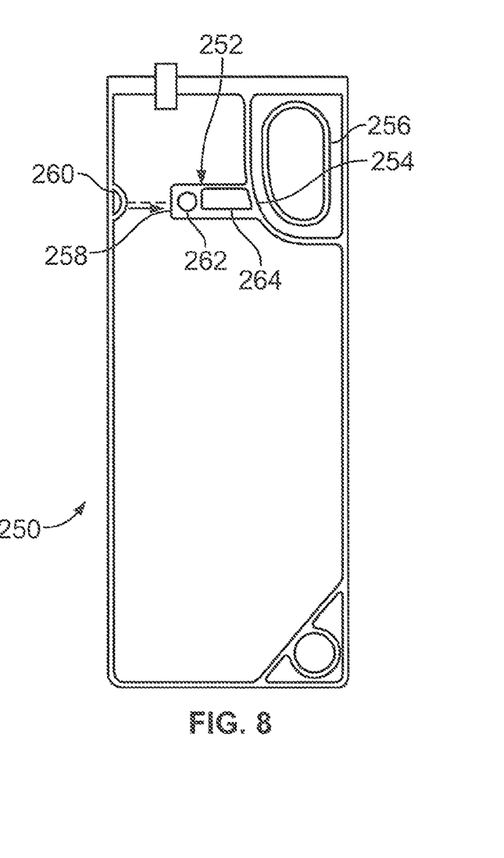
FIG. 8 is a front elevational view of yet another embodiment of a urinary collection bag or other receptacle according to an aspect of the present disclosure.

The bag 250 of FIG. 8 has a tear-stopping formation 252 that is a variation of the tear-stopping formation 202 of FIG. 7. In the embodiment of FIG. 8, the tear-stopping formation 252 is relatively wide compared to the tear-stopping formation 202 of FIG. 7, with a first end 254 positioned in approximately the same location as the corresponding end of the tear-stopping formation 202 of FIG. 7 (i.e., adjacent to the handle seal 256) and a second end 258 positioned closer to the tear-starting formation 260 than in FIG. 7. Due to the second end 258 being positioned relatively close to the tear-starting formation 260, the resulting spout that is formed when the bag 250 is torn by a user will be relatively narrow, which may be preferred for a more controlled release of urine from the bag 250.

The tear-stopping formation 252 of FIG. 8 also differs from the tear-stopping formation 202 of FIG. 7 in that it includes two openings 262 and 264, rather than a single opening. In the illustrated embodiment, the first opening 262 is substantially circular, while the second opening 264 is generally trapezoidal and more elongated than the first opening 262, but it should be understood that the openings 262 and 264 may be differently configured without departing from the scope of the present disclosure. Additionally, it should be understood that the openings 262 and 264 may be substantially identical, rather than being differently configured and/or the tear-stopping formation 252 may be provided with three or more openings. Further, it should be understood that a tear-stopping formation of this type is not limited to an adjoined tear-stopping formation (as in the illustrated embodiment), but may also be embodied as an isolated tear-stopping formation.

Figure 9:
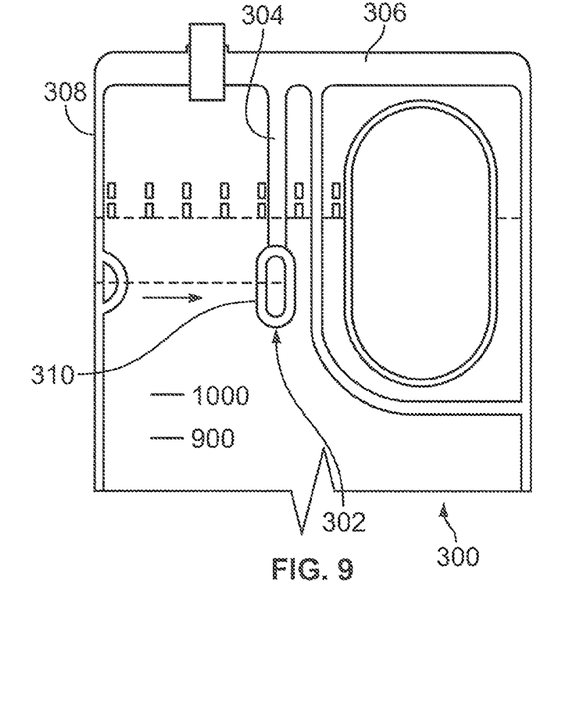
FIG. 9 is a detail view of a portion of another embodiment of a urinary collection bag or other receptacle according to an aspect of the present disclosure.

The bag 300 of FIG. 9 has a tear-stopping formation 302 that is a variation of the tear-stopping formation 62 of FIG. 4. In the embodiment of FIG. 9, an adjoining seal 304 extends from the end 306 of the peripheral seal 308 to the formation seal 310 of the tear-stopping formation 302. While the embodiments of FIGS. 5-9 show adjoined tear-stopping formations joined to the peripheral seal (along with the handle seal in the embodiment of FIGS. 5 and 6), it should be understood that it is also within the scope of the present disclosure for a tear-stopping formation to be joined by one or more adjoining seals to only the handle seal, without being joined to the peripheral seal.

Figure 10:
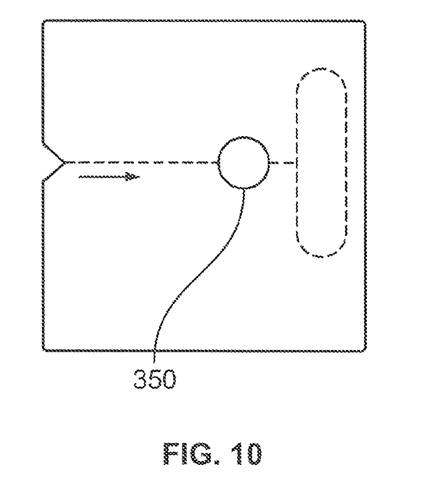
FIG. 10 is a schematic view of a urinary collection bag or other receptacle having a tear-stopping formation according to an aspect of the present disclosure.
Figure 11:
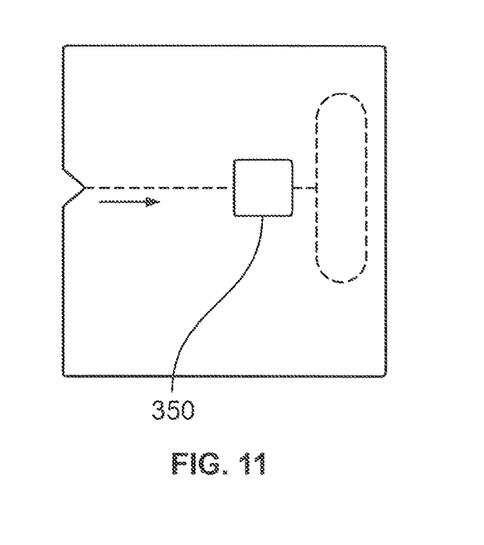
FIG. 11 is a schematic view of a urinary collection bag or other receptacle having another embodiment of a tear-stopping formation according to an aspect of the present disclosure.
Figure 12:
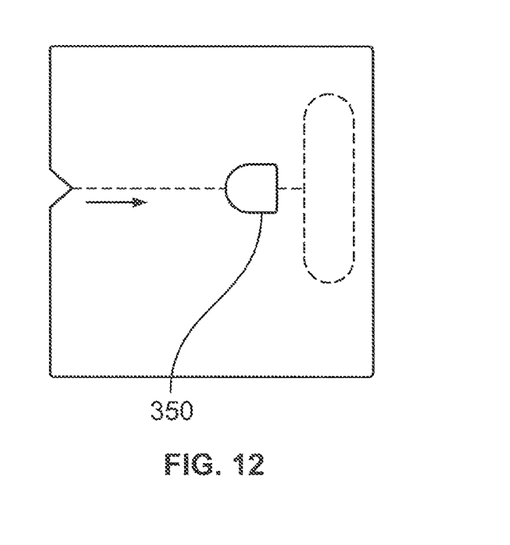
FIG. 12 is a schematic view of a urinary collection bag or other receptacle having yet another embodiment of a tear-stopping formation according to an aspect of the present disclosure.
Figure 13:
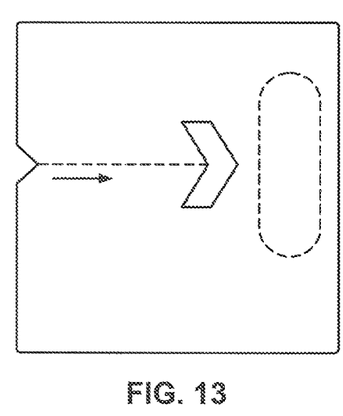
FIG. 13 is a schematic view of a urinary collection bag or other receptacle having another embodiment of a tear-stopping formation according to an aspect of the present disclosure.

FIGS. 10-23 illustrate alternative embodiments of tear-stopping formations that are differently configured from an opening surrounded by a formation seal (as in the embodiments of FIGS. 4-5 and 7-9) or a slit defined in a formation seal (as in the embodiment of FIG. 6). For example, FIG. 10 shows a tear-stopping formation 350 comprising a reinforcing material, which may have a greater tear resistance than the sheet material(s) defining the receptacle walls or at least combine with the one or both walls to provide the tear-stopping formation 350 with a greater tear resistance than the two sheet materials. In one embodiment, the reinforcing material is a polymer material having a greater tear resistance than the polymer material used to form the flexible walls. In another embodiment, the reinforcing material is the same material used to form the flexible walls, but has a greater thickness. In yet another embodiment, the reinforcing material is a non-polymer material having a greater tear resistance than the sheet material(s) of the walls. By providing a separate reinforcing material (rather than using the sheet materials to define the tear-stopping formation), a manufacturer may have more flexibility in terms of the characteristics of the tear-stopping formation. For example, the tear-stopping formation may be very thin and imperceptible to a user or, alternatively, may be colored or otherwise configured to be clear visual indicia to a user of where a tear is to terminate. In FIGS. 10-14, 20-23 (as in the previous Figures) the direction of the tear is identified by an arrow, and a handle opening is shown in broken lines.

Figure 14:
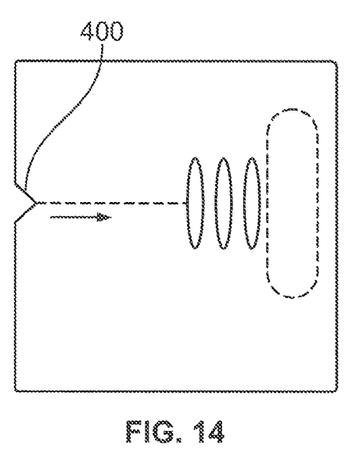
FIG. 14 is a schematic view of a urinary collection bag or other receptacle having yet another embodiment of a tear-stopping formation according to an aspect of the present disclosure.
Figure 15:
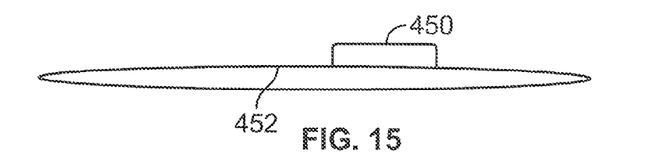
FIG. 15 is a top plan view of another embodiment of a urinary collection bag or other receptacle according to an aspect of the present disclosure.

The reinforcing material may be provided in any of a number of shapes and configurations, with FIGS. 10-14 showing exemplary shapes and configurations of the reinforcing material. The reinforcing material may be present in one location (as in FIGS. 10-13) or, as in FIG. 14, in multiple locations between a tear-starting formation 400 and at least a portion of a handle seal (which is shown in FIGS. 10-14, 21-22 in phantom lines). While FIG. 14 shows identical installations of reinforcing material in the various locations, it is also within the scope of the present disclosure for the installations of reinforcing material to be differently configured.

Figure 16:
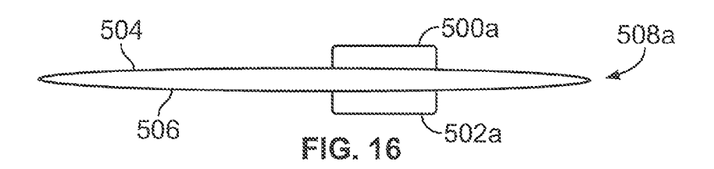
FIG. 16 is a top plan view of yet another embodiment of a urinary collection bag or other receptacle according to an aspect of the present disclosure.
Figure 17:
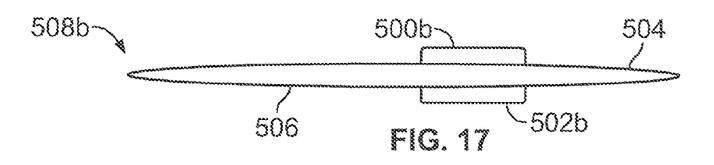
FIG. 17 is a top plan view of another embodiment of a urinary collection bag or other receptacle according to an aspect of the present disclosure.
Figure 18:
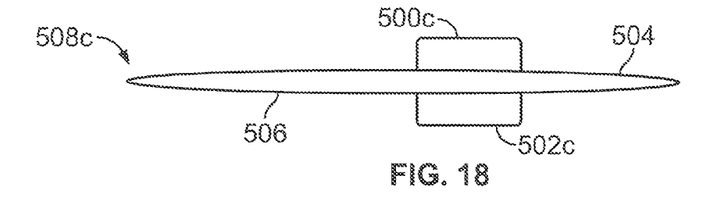
FIG. 18 is a top plan view of yet another embodiment of a urinary collection bag or other receptacle according to an aspect of the present disclosure.
Figure 19:
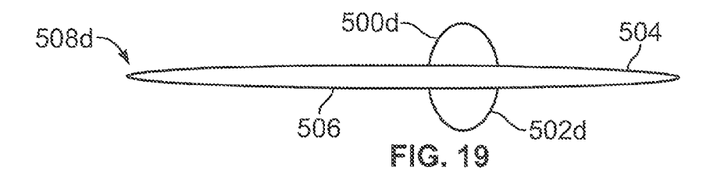
FIG. 19 is a top plan view of another embodiment of a urinary collection bag or other receptacle according to an aspect of the present disclosure.

The manner in which the reinforcing material is incorporated into the bag or other receptacle may vary, depending on the nature of the reinforcing material. For example, the reinforcing material may be secured to an outer surface of one or both of the flexible walls, as in FIGS. 15-19, FIG. 15 shows a reinforcing material 450 secured to one of the flexible walls 452, while FIGS. 16-19 each show a pair of reinforcing materials 500a-500d and 502a-502d, with one secured to each of the flexible walls 504 and 506. FIGS. 16-19 show bags 508a-508d in which the pair of reinforcing materials 500a-500d and 502a-502d are substantially identical to each other (with FIGS. 16-18 showing varying thicknesses and FIG. 19 showing a different shape) but, as noted above, it should be understood that a pair of reinforcing materials may be differently configured without departing from the scope of the present disclosure. A reinforcing material may be secured to an outer surface of a flexible wall in any suitable fashion, such as by being thermally bonded to the associated sheet material, secured thereto by an adhesive or an ultraviolet-curable coating, injection-molded onto the sheet material, or secured thereto using a mechanical fastener.

Figure 20:
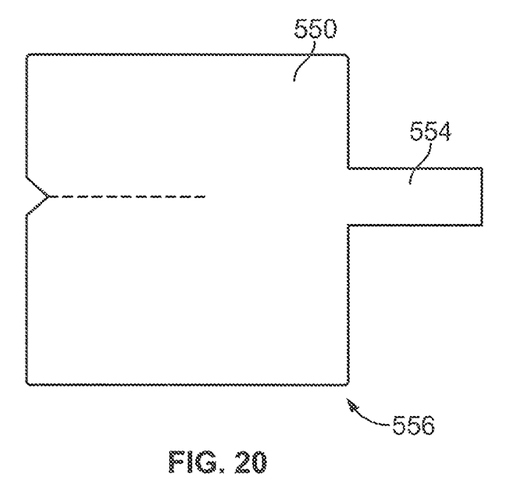
FIG. 20 is a schematic view of another embodiment of a urinary collection bag or other receptacle according to an aspect of the present disclosure, in a partially assembled condition.
Figure 21:
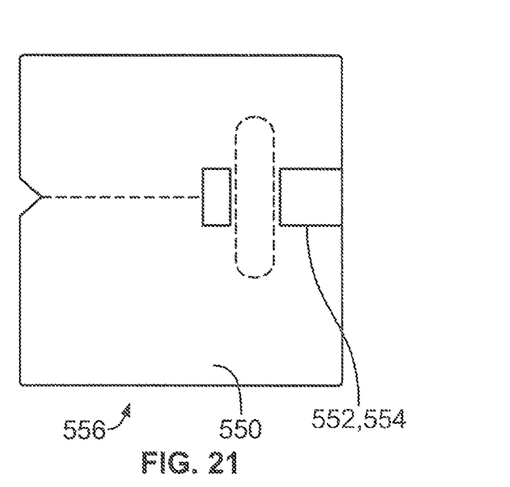
FIG. 21 is a schematic view of the urinary collection bag or other receptacle of FIG. 20, in an assembled condition.

FIGS. 20 and 21 illustrate one possible approach to securing a reinforcing material to an outer surface of a sheet material 550 to define a tear-stopping formation 552. In FIG. 20, one or both sheet materials 550 is provided with an extension or flap 554 that extends beyond what is to become the perimeter of the bag 556. The extension or flap 554 is folded back onto the wall 552 and secured thereto using any suitable approach to provide a reinforcing material which defines the tear-stopping formation 552, as in FIG. 21. Thus, in such an embodiment, the reinforcing material itself does not having a greater tear resistance than the sheet material of the wall(s), but rather combines with the flexible walls to provide the resulting tear-stopping formation 552 with an increased tear resistance. A handle opening 558 defined by a handle seal 560 may be provided after folding back and securing flap 554, as schematically shown in FIG. 21.

Figure 22:
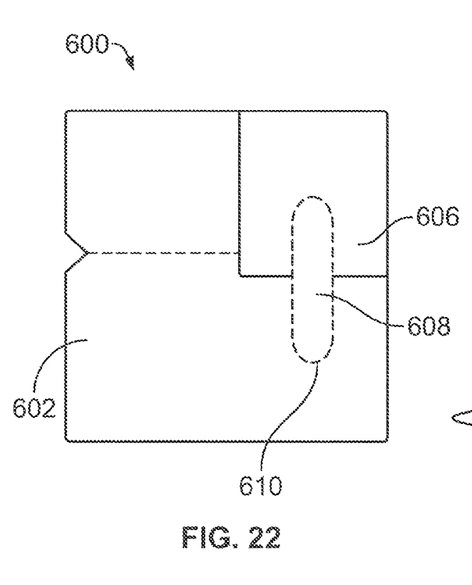
FIG. 22 is a schematic view of another embodiment of a urinary collection bag or other receptacle according to an aspect of the present disclosure.
Figure 23:
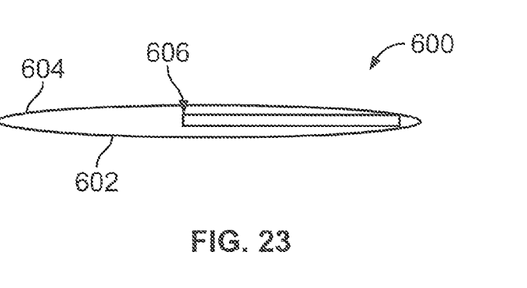
FIG. 23 is a top plan view of the urinary collection bag or other receptacle of FIG. 22.

FIGS. 22 and 23 illustrate an embodiment in which a reinforcing material is positioned within a bag 600, between the two sheet materials 602 and 604, and secured to one or both of the sheet materials 602 and 604 to define a tear-stopping formation 606. The reinforcing material may be secured to the sheet materials 602 and/or 604 using any suitable approach, including the ones described above with respect to a reinforcing material secured to an outer surface of a wall. In one exemplary embodiment, the reinforcing material comprises a layer of film material (which may be the same film material as the walls 602 and 604 or a different film material) that is bonded to inner surfaces of one or both of the sheet materials 602 and 604. A handle opening 608 defined by handle seal 610 may be provided through sheets 602/604 and tear-stopping formation 606, as shown in FIG. 22.

Figure 24:
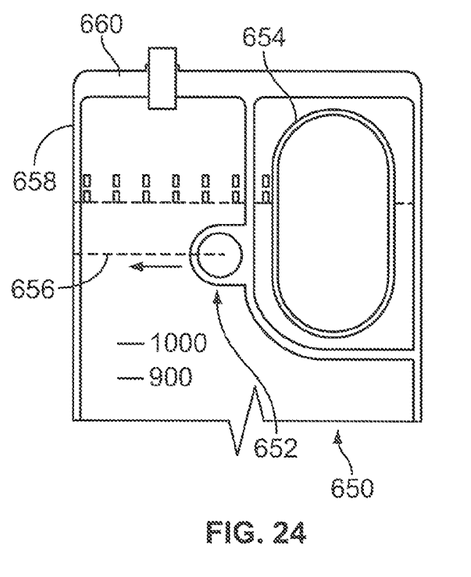
FIG. 24 is a detail view of a portion of another embodiment of a urinary collection bag or other receptacle according to an aspect of the present disclosure.
Figure 25:
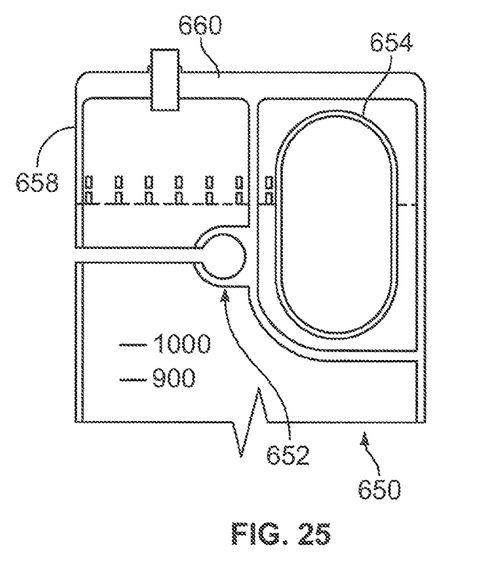
FIG. 25 is a detail view of the urinary collection bag or other receptacle of FIG. 24, showing a tear extending from a tear-starting formation to a peripheral seal.

FIGS. 24 and 25 illustrate an embodiment of a urinary collection bag or other receptacle 650 that may lack a tear-stopping formation or at least a tear-stopping formation positioned adjacent to a handle seal. In the embodiment of FIGS. 24 and 25, a tear-stopping formation of the type described above is replaced with a tear-starting formation 652 positioned adjacent to a handle seal 654. The tear-starting formation 652 may be variously configured without departing from the scope of the present disclosure, including being configured as either an adjoined tear-starting formation (consistent with the manner in which the term "adjoined" is used herein with respect to the configuration of a tear-stopping formation), as in FIGS. 24 and 25, or as an isolated tear-starting formation (consistent with the manner in which the term "isolated" is used herein with respect to the configuration of a tear-stopping formation), Regardless of the particular configuration of the tear-starting formation 652, the bag or receptacle configuration of FIGS. 24 and 25 reverses the direction in which a user creates a tear in the bag or receptacle 650, in that the tear begins at a location adjacent to the handle seal 654 (i.e., at the tear-starting formation 652) and is directed along a generally linear tear line 656 away from the handle seal 654 and through the edge 658 of the perimeter seal 660, as shown in FIG. 25. As in the earlier Figures, the direction of the fear is indicated by an arrow. By presenting a configuration requiring the user to propagate a tear away from the handle seal 654 rather than toward the handle seal 654, the risk of tearing through the handle seal 654 is eliminated.

Figure 26:
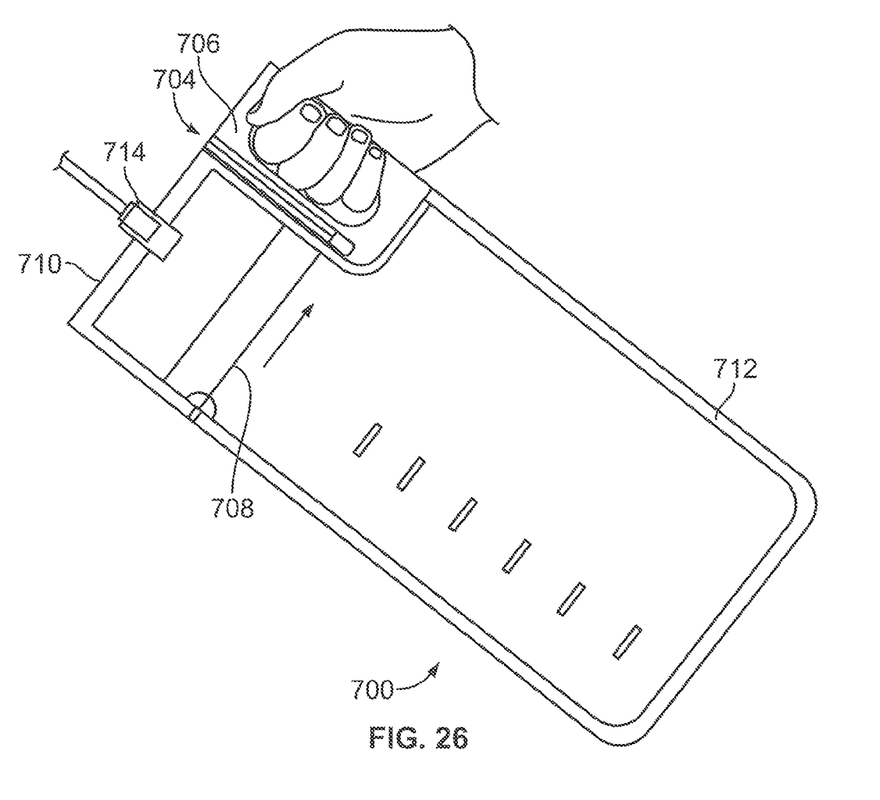
FIG. 26 is a front perspective view of another embodiment of a urinary collection bag or other receptacle according to an aspect of the present disclosure.
Figure 27:
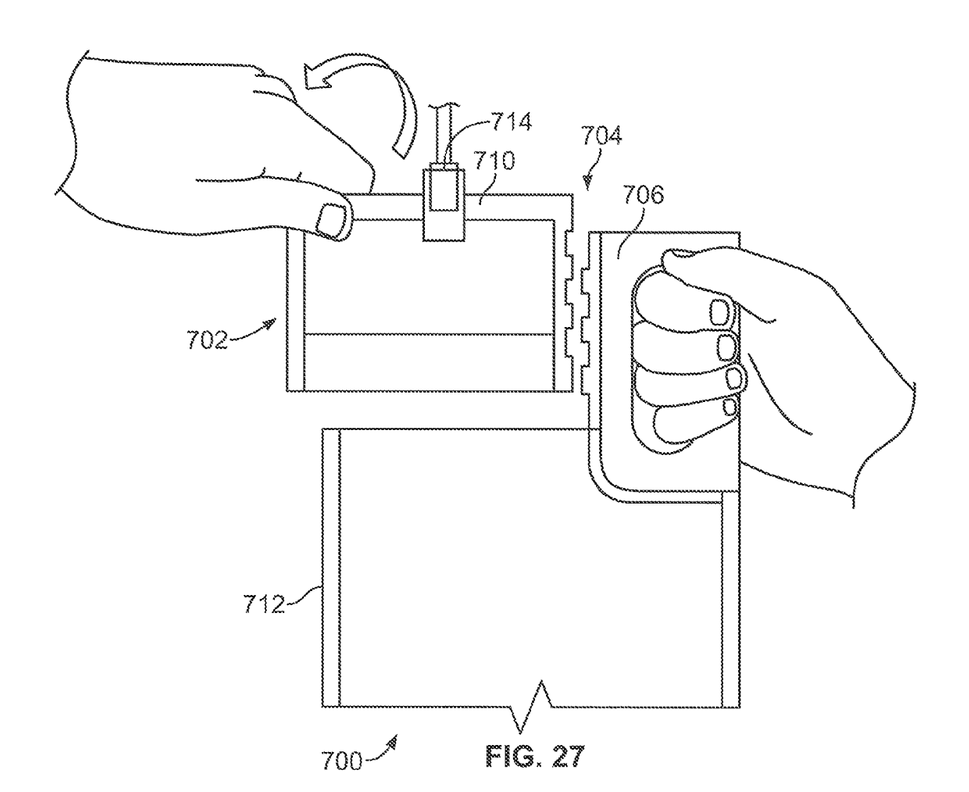
FIG. 27 is a detail view of a portion of the urinary collection bag or other receptacle of FIG. 26, showing a section of the bag broken away by a user.

FIGS. 26 and 27 illustrate an embodiment of a urinary collection bag or receptacle 700 in which a portion 702 thereof (FIG. 27) may be dissociated from the remainder of the bag or receptacle 700. The bag or receptacle 700 of FIGS. 26 and 27 is provided with a frangible region 704 formed in the handle seal 706 and extending from the tear line 708 to the end 710 of the perimeter seal 712. The frangible region 704 may be defined by a line of perforations or slits formed in the handle seal 706 or may comprise a relatively thin region of the handle seal 706 or may be made relatively weak, with a relatively low tear resistance according to any other suitable approach. As in the previously described embodiments, a user creates a tear in the bag or other receptacle 700 (FIG. 27) along the tear line 708 (FIG. 26) to create a spout for emptying urine from the bag or receptacle 700. Thereafter, the user breaks the frangible region 704 to dissociate a portion 702 of the bag or other receptacle 700 (in one embodiment, a corner portion of the bag or receptacle 700 which includes the port 714) before emptying urine from the bag or receptacle 700. The user has the option of not breaking the frangible region 704, thereby leaving the portion 702 attached as a torn flap, although it may be advantageous to remove the portion 702 to prevent it from inadvertently coming into contact with urine being emptied from the bag or receptacle 700.

Figure 28:
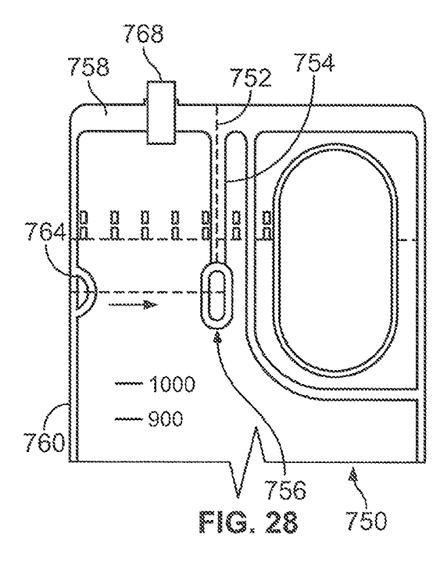
FIG. 28 is a detail view of a portion of another embodiment of a urinary collection bag or other receptacle according to an aspect of the present disclosure.
Figure 29:
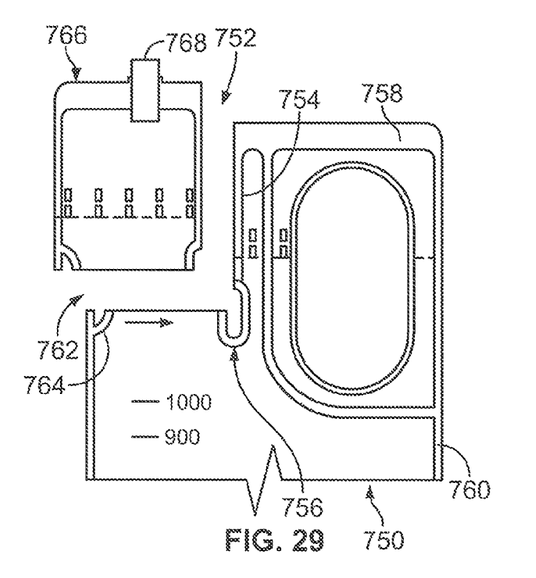
FIG. 29 is a detail view of a portion of the urinary collection bag or other receptacle of FIG. 28, showing a section of the bag broken away by a user.

FIGS. 28 and 29 illustrate a variation of the bag or other receptacle 300 of FIG. 9 and the bag or other receptacle 700 of FIGS. 26 and 27. The bag 750 of FIGS. 28 and 29 is configured as in FIG. 9, but a frangible region 752 (of the type described above with respect to FIGS. 26 and 27) is incorporated into the adjoining seal 754 extending from the tear-stopping formation 756 to the end 758 of the perimeter seal 760. A user creates a tear 762 (FIG. 29) from a tear-starting formation 764 to the tear-stopping formation 756 (as in the embodiment of FIG. 9) and may then break the frangible region 752 to dissociate a portion 766 of the bag or receptacle 750 (which portion 766 includes the port 768, in the illustrated embodiment) from the remainder of the bag or receptacle 750, while still maintaining the integrity of the handle opening. It should be understood that the embodiment of FIGS. 28 and 29 is merely exemplary and that other adjoined tear-stopping formations according to the present disclosure may also include a frangible region incorporated into an associated adjoining seal that extends to the peripheral seal.

In addition to providing collection bag with a spout for disposing of the urine, the embodiments of FIGS. 26-29 also provide the user with the option of disassociating the catheter (not shown) attached to port 714 (FIGS. 26-27) or port 768 from the bag before or after catheterization. Separating the catheter from the bag prior to catheterization allows the user to use the catheter only (and dispose of the urine directly into the toilet). Separation of the catheter from the bag may also provide more discreet disposal of the separated parts of the catheter assembly.

Figures 30, 31:
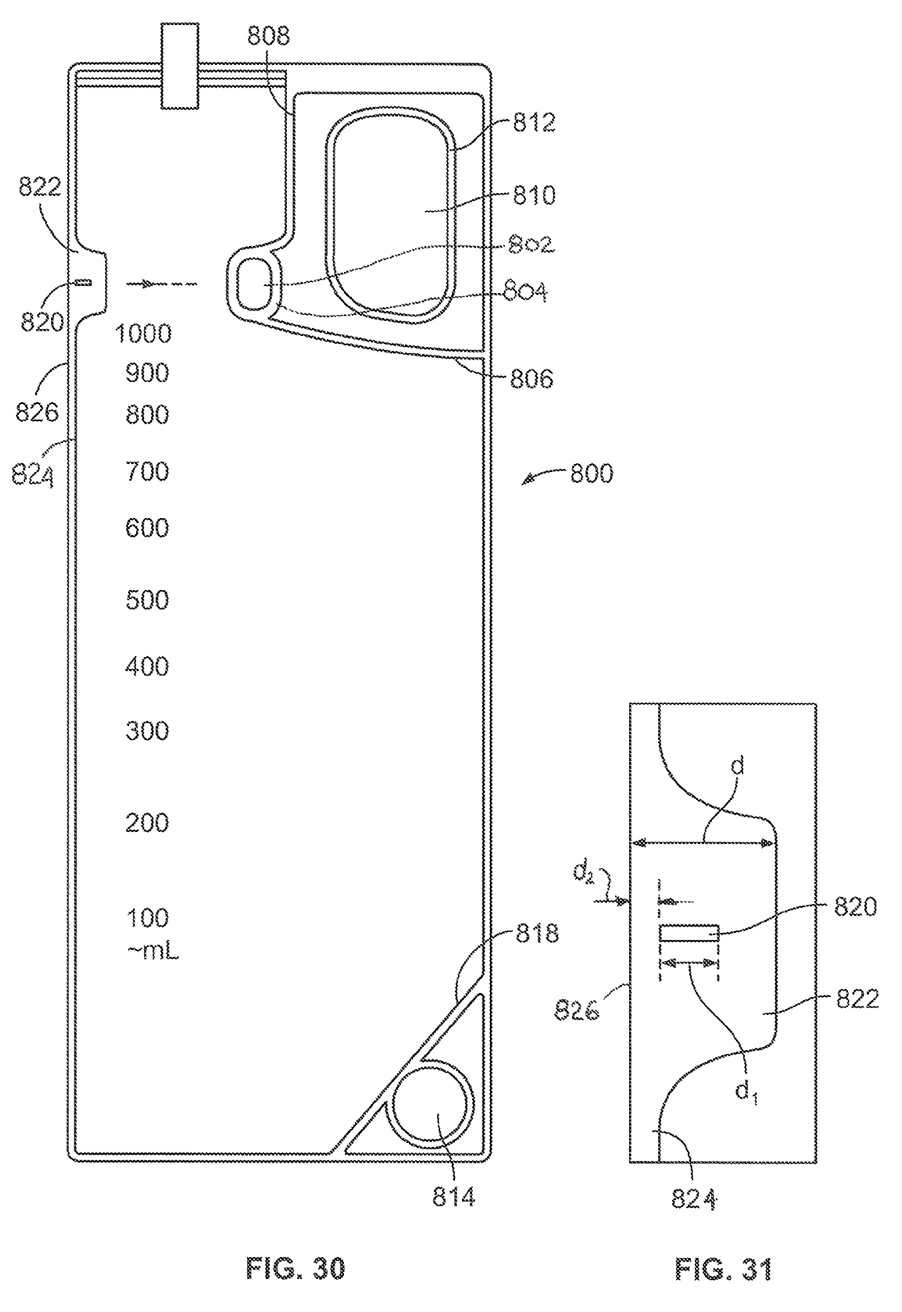
FIG. 30 is a front elevational view of a further embodiment of a urinary collection bag or other receptacle according to an aspect of the present disclosures.
FIG. 31 is an enlarged view of the tear-initiator portion of the collection bag of FIG. 30

FIGS. 30-31 illustrate another embodiment of a urine collection bag/receptacle 800. As shown in previous Figures, bag 800 includes a tear-stopping formation 802 at least partially defined by seal formation 804 and adjacent seals 806 and 808. Bag 800 may further include handle opening 810 defined by handle seal 812, Bag 800 may further include finger hole 814 defined by a corner hole seal 816 and sealed off from the interior chamber of bag 800 by seal line 818.

As shown in FIG. 30 and in greater detail in FIG. 31, bag 300 may include a tear initiator 820. Tear initiator 820 may be located within an expanded seal region 822 at the perimeter seal 824 of bag 800. Expanded seal region 822 may be continuous with perimeter seal 824 and extend inwardly in the direction of handle seal 812 by a distance "d." Tear initiator 820 may be defined by a perforation or through-hole in expanded seal region 822. Tear initiator 820 may be a rectangular or otherwise shaped perforation selectively spaced from the peripheral side edge 826 of bag 800. The selected spacing distance allows control of the tear force to initiate the tear through the sealed portion (e.g. expanded seal region 822) of bag 800. In one embodiment, distance $d_2$, the distance from the peripheral side edge to outer edge of tear initiator 820, may be approximately 2.0 mm±1.0 where the distance d of expanded seal region (from the peripheral side edge of the bag/receptacle 800 to its inward edge) is approximately 10.5 mm. The width of tear initiator ($d_1$) may be greater than the distance ($d_2$) from the edge 826 of bag 800 to the edge of tear initiator 820. Furthermore, the distance from the inner edge of tear initiator 820 to the inward edge of extended seal 822 may be greater than or equal to the width of the perimeter seal 824 of bag 800. The size of the tear initiator and its distance $d_2$ from the peripheral side edge 826 of bag 800 may vary depending on the dimensions and material of the bag.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A receptacle comprising top and bottom opposed ends and first and second opposed side edges, said receptacle further comprising:
    a first flexible wall having a perimeter;
    a second flexible wall having a perimeter;
    a perimeter seal joining at least a portion of the perimeter of the first flexible wall to at least a portion of the perimeter of the second flexible wall;
    a handle seal joining the first flexible wall to the second flexible wall and defining a handle opening spaced from said perimeter seal;
    a tear-starting formation defined in the perimeter seal; and
    a tear-stopping formation, wherein
        the tear-stopping formation is positioned between the tear-starting formation and at least a portion of the handle seal whereby
        the tear-stopping formation is configured to terminate a tear extending from the tear-starting formation toward the handle seal, and
        the tear-stopping formation comprises a reinforcing material having a greater tear resistance than the first and second flexible walls, wherein a first installation of a reinforcing material is secured to an outer surface of the first flexible wall and a second installation of a reinforcing material is secured to an outer surface of the second flexible wall.

2. The receptacle of claim 1, wherein the reinforcing material is secured to an outer surface of at least one of the first and second walls.

3. The receptacle of claim 1, wherein the first installation of the reinforcing material is substantially identically shaped to the second installation of the reinforcing material.

4. The receptacle of claim 1, wherein the first and second installations of the reinforcing material are shaped differently from each other.

5. The receptacle of claim 1, wherein the reinforcing material is secured to an inner surface of at least one of the first and second flexible walls.

6. The receptacle of claim 1, wherein the reinforcing material is secured to inner surfaces of the first and second flexible walls.

7. The receptacle of claim 1, wherein the reinforcing material is positioned at a plurality of locations positioned between the tear-starting location and at least a portion of the handle seal.

8. A receptacle comprising top and bottom opposed ends and first and second opposed side edges, said receptable further comprising:
    a first flexible wall having a perimeter;
    a second flexible wall having a perimeter;
    a perimeter seal joining at least a portion of the perimeter of the first flexible wall to at least a portion of the perimeter of the second flexible wall;
    a handle seal joining the first flexible wall to the second flexible wall and defining a handle opening spaced from said perimeter seal;
    a tear-starting formation defined in the perimeter seal; and
    a tear-stopping formation, wherein
        the tear-stopping formation is positioned between the tear-starting formation and at least a portion of the handle seal whereby
        the tear-stopping formation is configured to terminate a tear extending from the tear-starting formation toward the handle seal and wherein the tear-stopping formation is completely separated from the perimeter seal and from the handle seal by an unsealed section in which the first flexible wall is not joined to the second flexible wall.

9. A receptacle comprising top and bottom opposed ends and first and second opposed side edges, said receptacle further comprising:
    a first flexible wall having a perimeter;
    a second flexible wall having a perimeter;
    a perimeter seal joining at least a portion of the perimeter of the first flexible wall to at least a portion of the perimeter of the second flexible wall;
    a handle seal joining the first flexible wall to the second flexible wall and defining a handle opening spaced from said perimeter seal;
    a tear-starting formation defined in the perimeter seal;
    a tear-stopping formation, wherein
        the tear-stopping formation is positioned between the tear-starting formation and at least a portion of the handle seal whereby
        the tear-stopping formation is configured to terminate a tear extending from the tear-starting formation toward the handle seal; and
    an adjoining seal joining the first flexible wall to the second flexible wall, wherein the adjoining seal extends from the tear-stopping formation to the handle seal and to the perimeter seal.

* * * * *